United States Patent [19]

Kanai et al.

[11] Patent Number: 5,250,661
[45] Date of Patent: Oct. 5, 1993

[54] ESTABLISHED CELL LINE

[75] Inventors: Yoshiyuki Kanai, Tokyo; Akira Awaya, Yokohama, both of Japan

[73] Assignee: Mitsui Toatsu Chemicals Incorporated, Tokyo, Japan

[21] Appl. No.: 878,451

[22] Filed: May 5, 1992

Related U.S. Application Data

[60] Division of Ser. No. 798,043, Nov. 27, 1991, Pat. No. 5,132,222, which is a continuation of Ser. No. 651,118, Feb. 5, 1991, abandoned, which is a continuation of Ser. No. 917,056, Oct. 19, 1986, abandoned.

[30] Foreign Application Priority Data

Oct. 15, 1985 [JP] Japan ........................... 227709

[51] Int. Cl.$^5$ ................ C07K 13/00; C07K 15/00; C07K 15/06; A61K 37/02
[52] U.S. Cl. ..................... 530/351; 424/85.1; 424/85.7; 530/829; 530/868; 530/350
[58] Field of Search ............ 530/351; 435/69.5, 69.51, 435/69.52; 514/2, 8; 424/85.1, 85.7; 514/12

[56] References Cited

U.S. PATENT DOCUMENTS 5,132,222 7/1992 Kanagi et al. ............... 435/240.2

FOREIGN PATENT DOCUMENTS 60169424 of 0000 Japan .
0257406A2 3/1988 Japan .

OTHER PUBLICATIONS

A. Muraguchi, et al. J. Immunol, vol. 127, pp. 412–416. Aug. 1981.
T. Teranashi, et al. J. Immunol, vol. 128(4), pp. 1903–1908.
K. Takatsu, et al. J. Immunol., vol. 134(1), pp. 382–389.
Kanai, Y., et al., Int. Archs Allergy Appl. Immunol. 81: 92–4 (1986), "An established MRL/MP-lpr/lpr cell line with Nyll Cell properties produces a B cell differentiation factor(s) . . . ".
Kamai, Y., et al. Mol. Biol. Rep. 15(3–4):133 (1991) "Molecular Cloning of Nucleobindin, a novel 55 KD DNA-Binding Protein that Induces protection of IgG anti-DNA antibodies . . . ".
Kamai, Y. et al., Immuno Lett 32:43–48 (1992), "Purification of a novel B cell growth and differentiation factor associated with lupus syndrome".
Miura, K. et al., Biochem. Biophys Res. Comm. 187:375–80 (1992), "Molecular cloning of nucleobindin, a novel DNA-binding protein that contains both a signal peptide and a leucine-zipper Structure".
Kanai, Y. et al (II) "Establishment and Function of an MRL/MP-1pr1pr Lymphoma line with Null Cell Properties: Its Roles for Anti-DNA Antibody Production in vitro," In Kano et al (ed) *Cellular, Molecular and Genetic Approaches to Immunodiagnosis and Immunotherapy; VIIIth Internatonal Conference on Labeled Antibodies, Tokyo, Japan, No. 5–7, 1985, Karger, Basel, 1987*, pp. 283–288.
*Immunophysiology* "Interleukins and Interferons Acting on B Lymphocytes". R. L. Coffman et al. Oxford Univ. Press. 1990.
The Cytokine Handbook, Academic Press 1991 Chapter 9 Sanderson "Interleukin-7" pp. 149–190.
J. Immunol. vol. 134, No. 6, Jun. 1985, 3944–51 Harada et al "BCGFII Activity on Activated B Cells of a Purified etc".
Abstract JP 60-169424 Derwent.

Primary Examiner—Christine M. Nucker
Assistant Examiner—T. Cunningham
Attorney, Agent, or Firm—Nixon & Vanderhye

[57] ABSTRACT

B cell differentiation factor which acts on B cells and participates in their differentiation into antibody-producing cells is produced by an established cell line.

1 Claim, No Drawings

ESTABLISHED CELL LINE

CROSS-REFERENCE TO RELATED APPLICATIONS

This application is a division of application Ser. No. 07/798,043 filed Nov. 27, 1991, now U.S. Pat. No. 5,132,222 which in turn is a continuation of application Ser. No. 07/651,118 filed Feb. 5, 1991, abandoned, which is a continuation of Ser. No. 917,056 filed Oct. 19, 1986, abandoned.

BACKGROUND OF THE INVENTION

1. Field of the Invention

This invention relates to a novel established cell line. This cell line produces a soluble factor which acts on B cells and participates in their differentiation into antibody-producing cells. These antibodies are suitable for use in the diagnosis and treatment of rheumatism, autoimmune diseases, immunodeficiency, various infectious diseases, cancer and other diseases in man and animals. These antibodies are also useful as antigens for inducing the formation of anti-idiotype anitbodies thereto. Moreover, this cell line provides a means very useful, for example, for the analysis of the mechanisms involved in the development of autoimmune diseases, immunodeficiency and the mechanisms involved in the carcinogenesis and metastasis of cancer, and the like.

2. Description of the Prior Art

In order to elucidate the pathology and etiology of autoimmune diseases or the like and make use of the results in the treatment and diagnosis thereof, and in order to analyze the mechanism of immune reactions, an increasing number of studies are being made on animals with autoimmune disease, including mouse strains with autoimmune disease (for example, lupus mouse strains such as NZB mice, NZB/W Fl mice, MRL/MP-lpr/lpr (MRL/l) mice, MRL/Mp-+/+(MRL/n) mice, BXSB mice are known). In MRL/l mice, the lymph nodes begin to swell markedly at the age of about 10 weeks, and abnormal production of autoantibodies (in particular, anti-DNA antibodies) is observed, and lupus nephritis occurs at high rates.

As to the mechanism of antibody production, it has been elucidated that a soluble factor having the effect of inducing the differentiation of B cells is produced by T cells and takes part in the process in which the B cells having been stimulated to divide and grow and differentiate into antibody-producing cells (for example, Dutton, R. W., et al.: Prog. Immunol., 1, 355, 1971; and Schimpl, A., & Wecker, E.: Nature New Biol., 237, 15, 1972).

Such a factor is called T cell replacing factor (TRF). It is also known that this factor is produced by the mixed culture (MLR) of lymphocytes having different major histocompatibility antigens or by stimulating T cells with a mitogen such as Concanavalin A (Con A) or with non-specific antigens.

TRF is a humoral factor acting on B cells and it does not induce the proliferation of B cells, but induces the differentiation of B cells into antibody-producing cells. Accordingly, TRF is also called B cell differentiation factor (BCDF).

Conventionally known methods for the preparation of BCDF include the method of preparing BCDF by purification from the supernatant of a culture of a T cell hybridoma (Takatsu, K., et al., J. Imunol., 134, 382, 1985) and the method of producing human BCDF by use of cells derived from human B cells (Japanese Patent Laid-Open No. 169424/85).

As a differentiation factor which is produced without stimulation with a mitogen or antigen or without resorting to MLR, there has been reported one produced by T cells of the MRL/l mouse which is considered to be an animal model of human systemic lupus erythematodes (Prud'Homme, G. J., et al., J. Exp. Med., 157, 730, 1983).

Thus, the presence of various factors is known, but none of the cell lines or clones producing such factors have ever been established as cell lines having self-growing ability.

BCDF (TRF), together with anti-BCDF antibody, can be utilized in an immunoassay system for analyzing the pathological state of various diseases.

Moreover, BCDF (TRF) can also be utilized for the treatment of immunodeficiency in patients suffering from a reduction in the antibody-producing ability of B cells due to a malfunction of helper T cells.

Furthermore, a useful monoclonal antibody can be efficiently produced by culturing monocloned B cells in vitro and then stimulating their antibody production by the action of BCDF. This antibody can be utilized for the treatment and diagnosis of various diseases.

In view of the above-described usefulness of BCDF (TRF), it seems essential from an industrial point of view to obtain BCDF (TRF) in sufficient amounts, characterize it fully, and ensure industrial production thereof semipermanently. In the existing state of the art, however, BCDF-producing cell lines which have thus far been reported cannot produce BCDF stably and consistently. For example, BCDF (TRF) has neither been purified, identified or characterized fully, nor produced industrially, because no cell line of T cells capable of producing BCDF (TRF) has been established from the MRL/l mouse in the prior art.

Accordingly, it is of urgent necessity to establish a cell line which can produce BCDF (TRF) and can be stably subcultured for a long period of time.

SUMMARY OF THE INVENTION

The present inventors have thought that an animal with autoimmune disease will be one producing selectively and abnormally an antibody specific for an autoantigen and the analysis of the pathological state of such an animal will make it possible to elucidate the mechanism involved in the abnormal production of autoantibodies and the development of autoimmune diseases and thereby devise a means useful for the treatment of autoimmune diseases, cancer or the like. Specifically, judging from the fact that the swelling of lymph nodes in MRL/l mice is due mainly to the abnormal proliferation of Thyl$^+$, Lytl$^+$ T cells, the present inventors have established the hypothesis that these T cells of the lymph nodes are producing some factor acting stimulatively on the production of anti-nucleic acid antibodies or other autoantibodies.

On the basis of this hypothesis, the present inventors tried to make a long-term culture of lymph node cells collected from an MRL/l mouse, representative of animals with autoimmune disease, and have now succeeded in the establishment of a cell line (named KML$_1$) which acquired self-growing ability 8 months after the commencement of the culture.

Thus, the KML$_1$ cell line having self-growing ability has been established by culturing lymph node cells collected from an MRL/l mouse for a long period of time, and not by forming an artificial hybridoma on an extension of the prior art. In particular, it is an epoch-making finding that the KML$_1$ cell line consists of null cells, and this finding has not yet appeared in the literature.

Moreover, by examining the effect of the supernatant of a culture of the established cells of the present invention, or the established cells themselves, on the in vitro production of anti-DNA antibodies by MRL/l mouse spleen cells, it has been found that the production of anti-DNA antibodies is enhanced by a factor of 3 to 5. Further it has been found that the effect of the supernatant in vitro on the increase of the total number of antibody-producing cells for both IgG and IgM in spleen cells of MRL/l mice is above 2.5-fold. In addition, it has been made clear that the number of cells producing antibodies per unit population of spleen cells is doubled by administering the supernatant in combination with DNA to BALB/C mice previously immunized with DNA.

These results suggest that the KML$_1$ cell line of the present invention produces a factor (TRF or BCDF) participating in the differentiation of antibody-producing cells, thus leading to the attainment of the goal of the present invention. It has also been confirmed that this factor is not B cell growth factor (BCGF) because it does not stimulate the DNA synthesis of B cells. It has been one of aims of the present invention to obtain a stable cell line which can be subcultured for a long period of time and which can be subcultured even after freezing and thawing. The present inventors have accomplished this aim by establishing the KML$_1$ cell line having a self-growing ability, and have completed the present invention.

Accordingly, it is an object of the present invention to provide an established cell line having the ability to produce BCDF stably.

It is another object of the present invention to provide several methods by which the established cell line having the ability to produce BCDF can be applied to various uses.

These objects of the present invention can be accomplished by providing an established cell line (KML$_1$) obtained by (a) collecting lymphoid cells from a mouse or human patient with an autoimmune disease, (b) culturing the lymphoid cells in a culture medium containing the supernatant of a culture in which lymphoid cells of animal origin have been grown in the presence of a mitogen, and (c) repeating said step (b) by using a fresh culture medium as defined above.

The KML$_1$ cell line obtained in the above-described manner consists of cells that can grow stably both when subcultured repeatedly and when frozen, thawed and cultured again. Moreover, the KML$_1$ cell line has the ability to produce BCDF and, therefore, can be used to produce large amounts of BCDF on an industrial scale. Furthermore, the KML$_1$ cell line is also valuable in that it is possible to allow KML$_1$ cells to act on previously separated antigen-specific B cells and thereby cause the B cells to produce an antigen-specific antibody. In addition, the BCDF produced by the KML$_1$ cell line is potentially useful because, in some cases, it may act selectively on antigen-specific B cells alone and thereby cause them to produce only antibodies specific for the antigens.

In conventional cell fusion techniques, the frequency of formation of hybridomas producing a desired antibody can be improved by first culturing spleen cells from an immunized animal in the presence present invention to increase the number of antibody-producing cells, and then subjecting them to cell fusion.

On the contrary, an antibody specific for the aforesaid BCDF may be produced and used to inhibit the abnormal stimulation of antibody production. Moreover, it also becomes possible to seek for inhibitors of BCDF, and this will open the way for the development of a new treatment. In addition, because of the outstanding feature that the KML$_1$ cell line has a self-growing ability, they can be used as parent cells (or partner cells) into which various cells can be fused. The formation of useful hybridomas makes it possible to produce a variety of useful physiologically active materials and monoclonal antibodies.

Thus, by elucidating various properties of the KML$_1$ cell line of the present invention and by using various factors including BCDF obtained with the KML$_1$ cell line, it becomes possible to analyze more accurately the mechanisms of autoimmune diseases, immunodeficiency, carcinogenesis, metastasis of cancer and the like. Accordingly, the KML$_1$ cell line of the present invention provides a means very useful for the diagnosis and treatment of various diseases.

DETAILED DESCRIPTION OF THE INVENTION AND PREFERRED EMBODIMENTS

The established cell line of the present invention can be obtained by (a) collecting lymphoid cells from a mouse or human patient with autoimmune disease, (b) culturing the lymphoid cells in a culture medium containing the supernatant of a culture in which lymphoid cells of animal origin have been grown in the presence of a mitogen, and (c) repeating the step (b) by using a fresh culture medium as defined above.

The present invention will be more specifically described below in connection with an embodiment in which an MRL/l mouse is used as the mouse with the autoimmune disease and mesenteric lymph node cells are used as the lymphoid cells for the establishment of cell line in the long-term culture of cells.

A single cell suspension (SCS) is prepared by collecting mesenteric lymph node cells from a female MRL/( mouse, aged 20 weeks, and suspending these cells in Dulbecco's modified Eagle medium (DMEM) for the cultivation thereof.

In addition to DMEM, RPMI 1640, MEM and like media may be used for the preparation of SCS. Moreover, serum-free media can also be used for the establishment of the cell line and the cultivation of the established cells. For example, serum-free media such as Hybrity-1 (manufactured by Sanko Junyaku K. K.) and the like may preferably be used to achieve satisfactory cultivation of the established cells.

The aforesaid culture medium further contains the following additives.

| Additive | Concentration |
| --- | --- |
| Bovine fetal serum inactivated by heating at 56° C. for 30 minutes (FCS; manufactured by Gibco) | 1–20%, preferably 5% |
| Penicillin | About 10–250 units/ml, preferably about 100 units/ml |
| Streptomycin | About 10–250 μg/ml, preferably about |

-continued

| Additive | Concentration |
| --- | --- |
|  | 100 g/ml |
| 2-Mercaptoethanol | 50 μM |
| Hepes buffer solution | 10 mM |
| L-glutamine | 0.5-10 mM, preferably 2 mM |

In the long-term culture of T cells, it is common practice to add interleukin-2 (IL-2) to the culture medium. In the practice of the present invention, the supernatant of a culture in which lymphoid cells of animal origin are grown in the presence of a mitogen is added, as an additive corresponding to IL-2, to the culture medium for the cultivation of mesenteric lymph node cells from an MRL/l mouse. This supernatant can be obtained by collecting spleen cells from a female DBA/2 mouse, aged 4-6 weeks; suspending them in DMEM containing the aforesaid additives to form a cell suspension having a cell density of $2 \times 10^6$ cells/ml; adding thereto 2.5 μg/ml of Concanavalin A (Con A) (an exemplary of mitogen); incubating the cell suspension at 37° C. for 24 hours in an incubator having a 5% $CO_2$ atmosphere; separating the supernatant of the SCS; and then sterilizing the supernatant by filtration through a filter having a pore size of 0.2 μ (manufactured by Gelman). This procedure is described in an article by Gills et al. (Gills, S., et al.: Nature, 268, 154, 1977).

This sterilized filtrate (hereinafter referred to as CAS) is used as an alternative to IL-2. It may be stored in a frozen state at −70° C. and thawed just prior to use.

The established cell line of the present invention can be obtained by using the SCS and CAS prepared in the above-described manner.

First of all, 10% CAS is added to the aforesaid SCS in DMEM containing 5% FCS or in serum-free medium Hybrity-1, and the lymph node cells from MRL/l mice are cultured. The cell density in this culture medium should be of the order of $2 \times 10^6$ cells/ml.

The culture is carried out, for example, by placing 10 ml of the SCS in a 25 $cm^2$ flask (No. 25100; manufactured by Corning Glass Works). At intervals of 3 days, all cells are collected by centrifugation at 150xg for 5 minutes and transferred to a fresh culture medium, and no subculture is made until the cells increase in size and come to grow stably. Three months after the start of the culture, the process of transferring the cells to a fresh culture medium at intervals of 3 days is still continued.

Six months after the start of the culture, the cells are transferred to a 24-well culture plate (No. 3424; manufactured by Coaster) and cultured at a cell density of $5 \times 10^5$ cells/ml (2 ml in each well).

Subsequently, as soon as the growth of the cells is improved, the cells can be cultured in a large-sized flask such as a 75 $cm^2$ flask (No. 25110; manufactured by Corning Glass Works). Usually, the growth of the cells is improved 8 months after, the start of the culture. At this point in time, the cells acquire self-growing ability and become able to grow in the absence of CAS. These cells have a doubling time of about 14 hours. The established cell line thus obtained will hereinafter be referred to as the $KML_1$ cell line.

Features of the $KML_1$ Cell Line

The $KML_1$ cell line is a stable one. Its stability has been demonstrated by the fact that, when some cells of the KML1 cell line being cultured were frozen in liquid nitrogen at −140° C., stored in the frozen state for 3 months, and then returned to the culture system, they grew normally.

One year after the start of the culture, the cell-surface antigens of the $KML_1$ cell were determined by using antibodies specific for various lymphocyte markers. More specifically, using FITC-labeled antibodies or FITC-labeled biotin-avidin systems (in which the antibody is combined with the biotin and the avidin is labeled with FITC), the cell-surface antigens were detected by laser flow fluoro cytometry (SPECTRUM II; manufactured by Ortho). Thus, the $KML_1$ cell has been found to be Thy$l^-$, Lytl$^-$, Lyt2$^-$ and sIg$^-$ (surface immunoglobulin-negative), indicating that the $KML_1$ cell is the so-called null cell.

Moreover, its H-2 haplotype is k, indicating that the $KML_1$ cell is derived from the MRL/l mouse. The $KML_1$ cell is Ia-positive.

Furthermore, when tested according to the EA rosette method (Hudson, L., & Hay, F. C., Practical Immunology, Blackwell, Oxford, 1980), the $KML_1$ cell is Fc receptor-negative (FcR$^-$). When $KML_1$ cells are transplanted to nude mice (BALB/c-nu/nu), the formation of lymphomas is observed. Thus, it has been confirmed that $KML_1$ cells can take as tumor cells in nude mice.

B Cell Differentiation Factor (BCDF) Produced by the $KML_1$ Cell Line a) Preparation of a solution containing BCDF The $KML_1$ cell line of the present invention has the function of producing BCDF, and can be used to prepare a solution containing BCDF (hereinafter referred to as a BCDF solution). One typical procedure is described below.

In a flask having a capacity of 75 $cm^2$ (No. 25110; manufactured by Corning Glass Works), $KML_1$ cells are suspended in DMEM containing 5% FCS or in serum-free medium Hybrity-1 so as to give a cell density of $5 \times 10^6 - 10^7$ cells per culture. The resulting SCS is incubated at 37° C. for 24-48 hours in an incubator having a 5% $CO_2$ atmosphere. Immediately after completion of the incubation, the SCS is centrifuged at 2,500 rpm for 5 minutes, and the supernatant is separated and filtered through a 0.2 μ sterilizing filter (Acrodisk; manufactured by Gelman Co.) to obtain a BCDF solution. In the case when a BCDF solution is injected into animals, a concentrated BCDF solution can be further prepared by concentrating a supernatant separated by centrifuging in the above manner to one tenth of its original volume by using Aquacide III manufactured by Calbiochem), thoroughly dialyzing the resulting concentrated BCDF solution against DMEM and sterilizing it by filtration.

b) Determination of the B cell-differentiating effect (or the stimulative effect on antibody production by B cells)

The effect on B cell differentiation of BCDF present in the BCDF solution obtained in the above section a) can be determined according to the following procedure.

A series of culture media are prepared by adding various amounts of the BCDF solution in DMEM containing 5% FCS and the other additives listed above. Spleen cells obtained from a female MRL/l mouse, aged 4 months, are suspended in each of the culture media so as to give a cell density of $10^6$ cells/ml, and then cultured for 4 days. As a representative of the anti-nucleic acid antibody titer per unit protein concentration, the anti-single stranded (ss) DNA antibody titer of the 50% saturated ammonium sulfate fraction of the supernatant of each culture is determined and compared with control. The concentration of the antibody protein is determined by taking a 5-ml aliquot of the aforesaid supernatant, adding thereto an equal volume of a saturated ammonium sulfate solution to obtain a 50% saturated ammonium sulfate fraction, centrifuging the mixture at 17,000 rpm for 3 minutes at 2° C. on a microfuge (Model 780 Haemofuge; manufactured by Heraeus), and then measuring the absorbance ($A_{280}$) of the resulting supernatant at a wavelength of 280 nm. The activity of the antibody is determined according to the enzyme-linked immunosorbent assay and, basically, the procedure described in Japanese Patent Laid-Open No. 56694/'83, Japanese Patent Application No. 108642/'84 and Japanese Patent Application No. 60970/'85 is employed. Specifically, an ssDNA antigen is prepared by heating dsDNA at 100° C. for 5 minutes and then cooling it rapidly. In the wells of a micro titer plate (Immulon No. 2; manufactured by Dynatech) having ssDNA adsorbed thereon, 50 μl each of the aforesaid 50% saturated ammonium sulfate fractions were placed. After the plate is shaken at room temperature for an hour, it is washed three times with Tween/TBS (sodium chloride-containing Tris buffer solution/25 mM Tris hydrochloride +140 mM sodium chloride, pH 7.4) to remove any unreacted antibodies. Then, 50 μl of anti-mouse (IgG-+IgM) alkaline phosphatase conjugate (manufactured by Sigma) is added to each well, and the plate is similarly shaken at room temperature for an hour to effect the reaction. Thereafter, the plate is washed three times with Tween/TBS and 100 μl of a 2.5 mM p-nitrophenyl phosphate solution (prepared by dissolving P-NPP in a 50 mM sodium carbonate buffer solution, pH 9.5, containing 2 mM $MgCl_2$ so as to give a concentration of 1 mg/ml) is added to each well as a substrate of the enzyme. Then, the plate is incubated in an incubator at 37° C. for 60 minutes. Thus, the activity of the antibody combined with the antigen adsorbed on the plate can be determined by using the activity of the alkaline phosphatase-conjugated second antibody as an index. This enzyme activity can be determined, for example, by measuring the absorbance ($A_{405}$) at a wavelength of 405 nm with a Titertech Multiscan Autoreader (manufactured by Flow Laboratories).

When determinations were actually made according to the above-described procedure (Experiment 2), it was found that the in vitro production of anti-ssDNA antibody by MRL/1 mouse spleen cells was enhanced by a factor of about 3. In this testing system employed by the present inventors, an increase in the amount of antibody, and not an increase in the number of antibody-producing cells, is determined directly. Thus, the three-fold increase in the amount of antibody production is considered to be quite significant.

Moreover, the BCDF solution obtained by using the $KML_1$ cell line of the present invention has the effect of stimulating the differentiation of B cells and increasing the number of antibody-producing cells.

The ability of the BCDF solution to increase the number of antibody-producing cells can be tested, for example, according to the following procedure.

A series of culture media are prepared by adding various amounts of the BCDF solution obtained in the above section a) to the serum-free medium Hybrity-1. In these culture media, spleen cells obtained from a male MRL/1 mouse, aged 5 months, are suspended so as to give a cell density of $10^6$ cells/ml, and incubated for 4 days.

After completion of the incubation, the number of plaque forming cells (PFCs) in each culture is determined. Then, the ability of the BCDF solution to increase the number of antibody-producing cells can be evaluated on the basis of the relationship between the number of PFCs and the amount of BCDF solution added.

The number of PFCs is obtained by determining the total number of cells producing antibodies including both IgG and IgM. Generally, PFC assays are made according to the procedure of Gronovicz et al. (Gronovicz, E., et al.: Eur. J. Immunol., 6, 588–590, 1976). The number of ssDNA-specific PFCs can be determined according to the procedure of Roder et al. (Roder, J. C., et al.: J. Immunol., 121, 29–37, 1978).

As described in Experiment 5 which will be given later, when the BCDF solution was tested in vitro, the number of antibody-producing cells per unit population of MRL/1 mouse spleen cells was increased by a factor of above about 2.5. This increase in the number of antibody-producing cells indicates a parallel relationship with the above-described increase in the amount of antibody production.

The BCDF solution obtained with the $KML_1$ cell line of the present invention has the effect of stimulating in vivo the differentiation of B cells.

This in vivo effect can be tested, for example, according to the following procedure.

On the first day (=day 1) of the test, female BALB/c mice, aged 5 months, are immunized by intravenous injection of $4 \times 10^8$ ssDNA-coated sheep red blood cells (SRBCs). On day 4, $4 \times 10^8$ ssDNA-coated SRBCs are intravenously injected again and, at the same time, 0.2 ml of a BCDF solution is intraperitoneally administered to the mice. This BCDF solution is prepared by culturing $KML_1$ cells in the Hybrity-1 medium for 24 hours, concentrating the supernatant of the resulting culture to one tenth of its original volume by means of Aquacide III, dialyzing the concentrated solution thoroughly against DMEM, and then sterilized it by filtration. Similarly, 0.2 ml of the BCDF solution is intraperitoneally administered to the mice on days 6 and 8.

On day 10, spleen cells are collected from the BALB/c mice and the number of PFCs per unit population of spleen cells is determined according to the above-described procedures. As described in Experiment 6 which will be given later, when spleen cells were collected from the BALB/c mice and examined, it was found that the number of IgG PFCs per unit population of spleen cells was approximately doubled. This indicates that the number of antibody producing cells can actually be increased by in vivo administration of the BCDF solution.

c) Determination of the presence or absence of a B cell growth factor

The presence or absence of a B cell growth factor in the supernatant of a culture of $KML_1$ cells can be determined as follows.

A series of single cell suspensions containing spleen cells obtained from a female MRL/( mouse, aged 4 months, are prepared. After the addition of various amounts of the BCDF solution obtained in the above section a), the suspensions are incubated for 3 days. 18 hours before completion of the incubation, $^3H$-thymidine is added to the cultures in an amount of 1 μCi/ml.

After completion of the incubation, the cells are collected from each culture and tested to determine whether or not the incorporation of $^3$H-thymidine was enhanced by the addition of the BCDF solution.

When a determination was actually made according to the above-described procedure, it was found that the addition of a BCDF solution did not enhance the incorporation of $^3$H-thymidine. This indicates that the B cell growth activation factor is not present in the supernatant of a culture of KML$_1$ cells.

Enhancement of the Production of anti-DNA Antibodies by the mixed culture of MRL/l or MRL/n Mouse Spleen Cells with KML$_1$ Cells The KML$_1$ cell line having the above-described features can be used in a variety of applications. One exemplary application utilizing the direct effect of the KML$_1$ cell line is a method for enhancing the production of anti-DNA antibodies by the mixed cultivation (MLR) of MRL/l or MRL/n mouse spleen cells with KML$_1$ cells.

Actually, as described in Experiments 3 and 4 which will be given later, KML$_1$ cells and spleen cells obtained from a female MRL/l mouse, aged 4 months, or a female MRL/n mouse, aged 9 months, were cultured in a mixed state. MRL/n mouse is a mouse which is conjenic with MRL/l mouse, has a deletion of the lpr gene, and does not develop early symptoms of SLE (e.g., swelling of lymph nodes) unlike MRL/l mouse, but exhibits the production of anti-nucleic acid antibodies after a year (see Masanori Shiraki and Michio Fujiwara Rinsho Men'eki, 15, 15, 1983).

In the mixed culture of MRL/l mouse spleen cells with KML$_1$ cells, the in vitro production of anti-ssDNA antibody was enhanced by a factor of about 5 as compared with the cultivation of spleen cells alone, and the degree of enhancement was higher than that achieved by using the BCDF solution (see Experiment 3).

Also in the mixed culture of MRL/n mouse spleen cells with KML$_1$ cells, the production of anti-ssDNA antibody was enhanced (see Experiment 4). This result can be interpreted as follows: It is imagined that MRL/n mice do not develop the symptoms of SLE because the lpr gene which considered to participate in the abnormal proliferation of T cells is deleted. However, when MRL/n mouse lymphocytes are grown in the presence of KML$_1$ cells, a factor in which the lpr gene is thought to be reflected is produced by the KML$_1$ cells and, therefore, the antibody production by the lymphocytes is enhanced by the action of this factor.

On the basis of these considerations, BCDF produced by the KML$_1$ cell line of the present invention is thought to be applicable to the treatment of immunodeficiency patients characterized by reduced ability to produce antibodies.

The present invention has been described in connection with an embodiment in which the MRL/l mouse is used as the mouse with autoimmune mouse and meseteric lymph node cells are used as the lymphoid cells. However, the materials used for obtaining the established cell line of the present invention are not limited thereto. For example, the following materials may also be used.

Useful lymph node cells include, in addition to meseteric lymph node cells, for example lymph node cells collected from the submandibular lymph nodes, subaxillary lymph nodes, and inguinal lymph nodes. As the lymphoid cells collected from a mouse or human being with autoimmune disease, there may be used, in addition to lymph node cells obtained from MRL/l mice, lymph node cells, for example, obtained from NZB mice, NZB/W Fl mice, BXSB mice, New Zealand mice, SL/Ni mice and the like, as well as peripheral blood lymphocytes, tonsillar lymphoid cells, spleen cells and like cells obtained from human patients with autoimmune disease. Moreover, in order to obtain the supernatant (such as CAS) of a culture in which lymphoid cells of animal origin have been grown in the presence of a mitogen, there may used, in addition to spleen cells and lymph node cells obtained from DBA/2 mice, spleen cells and lymph node cells obtained from BALB/c mice, C3H/He mice, C57BL/6 mice, etc.; spleen cells and lymph node cells obtained from Wistar rats, Donryu rats, SD rats, etc.; spleen cells and lymph node cells obtained from guinea pigs, rabbits, dogs, cats, etc.; peripheral blood lymphocytes, spleen cells and lymph node cells obtained from human subjects; and the like.

The present invention relating to the establishment of the KML$_1$ cell line having the above-described properties and the production of BCDF is further illustrated by the following examples and experiments. However, it is to be understood that the present invention is not limited thereto.

EXAMPLE 1

Establishment of the KLM$_1$ Cell Line

A single cell suspension (SCS) was prepared by obtaining cells of mesenteric lymph nodes from a female MRL/l mouse, aged 20 weeks, and suspending them in DMEM containing 5% FCS and the other additives as described above at a cell density of $2 \times 10^6$ cells/ml.

Separately, spleen cells were obtained from a female DBA/2 mouse, aged 5 weeks, and suspended in DMEM containing 5% FCS and the other additives as described above to form a cell suspension having a cell density of $2 \times 10^6$ cells/ml. After the addition of 2.5 μg/ml of Con A, the cell suspension was incubated at 37° C. for 24 hours in an incubator having an 5% $CO_2$ atmosphere. Then, the supernatant of the resulting culture was sterilized by filtration through a 0.2 μ Acrodisk filter (manufactured by Nalgen).

This sterilized filtrate (CAS) was added to the SCS of the lymph node cells of the MRL/l mouse in an amount of 10%. Ten milliliter of the resulting mixture was placed in a 25 cm$^2$ flask (No. 25110; manufactured by Corning Glass Works) and the culture was started. At intervals of 3 days, all cells were collected by centrifugation at 150xg for 5 minutes and transferred to a fresh culture medium, and no subculture was made until the cells increased in size and came to grow stably. Three months after the start of the culture, all the cells increased in size, but still continued to grow slowly. Thus, the process of transferring the cells to a fresh culture medium at intervals of 3 days was continued. Six months after the start of the culture, the cells were transferred to a 24-well culture plate (No. 3424; manufactured by Coaster) and cultured at a cell density of $5 \times 10^5$ cells/ml (2 ml in each well). At this stage, the growth of the cells was improved and, thereafter, the cells became to grow in a 75 cm$^2$ large-sized flask (No. 25110; manufactured by Corning Glass Works). At this point in time, or 8 months after the start of the culture, these cells became able to grow in the absence of CAS and were judged to have acquired a self-growing ability. The cell line thus obtained was named $KML_1$. (A stock of the novel cell clone was deposited in the name of KANAI MRL-One-Seven ($KML_1$-7) in the European Collection of Animal Cell Cultures (ECACC), PHLS Center for Applied Microbiology & Research, Porton Down, Salisbury, Wiltshire SP4 0JG, United Kingdom, on September 18, 1986 and provisionally given the accession No. 86 091801.)

EXAMPLE 2

Culture of $KML_1$ Cells After Freezing and Thawing $KML_1$ cell were frozen in liquid nitrogen at $-140°$ C. and stored in the frozen state. After a month, the cells were thawed and cultured again. These cells grew stably and exhibited the same properties as those being subcultured.

EXAMPLE 3

Formation of Lymphomas in Nude Mice $10^7$ $KML_1$ cells were injected into the abdominal cavity of female nude mice (BALB/c-nu/nu). After 2 months, the formation of lymphomas was observed. Thus, it has been confirmed that $KML_1$ cells can take as tumor cells in nude mice.

EXAMPLE 4

Preparation of a BCDF Solution

In a 75 $cm^2$ flask (No. 25110; manufactured by Corning Glass Works), $KML_1$ cells were suspended in DMEM containing 5% FCS and the other additives as described above in an amount of $5 \times 10^6 - 10^7$ cells per culture, and grown at 37° C. for 48 hours in an incubator having a 5% $CO_2$ atmosphere. Immediately after that, the resulting culture was centrifuged at 2,500 rpm for 5 minutes. The supernatant was separated and sterilized by filtration through a 0.2 $\mu$ Acrodisk filter to obtain a BCDF solution.

EXAMPLE 5

Preparation of a BCDF Solution

The procedure of Example 4 was repeated except that the DMEM was replaced by the serum-free medium Hybrity-1 and the $KML_1$ cells were grown for 24 hours instead of 48 hours. The supernatant of the resulting culture was separated and sterilized by filtration.

EXAMPLE 6

Preparation of a Concentrated BCDF Solution

Using Aquacide III, the supernatant obtained in Example 5 was concentrated to one tenth of its original volume. The resulting concentrated BCDF solution was thoroughly dialyzed against DMEM and then sterilized by filtration in the same manner as described in Example 4.

EXPERIMENT 1

Analysis of Cell-Surface Antigens

Using antibodies specific for various cell-surface markers of lymphocytes, i.e., anti-Thy1 antibody (manufactured by Miles-Yeda), anti-Lyt1 antibody, anti-Lyt2 antibody (both manufactured by Becton-Dickinson) and anti-IgM antibody (manufactured by Department of Immunology, Institute of Medical Science, University of Tokyo), the cell-surface antigens of the $KML_1$ cell were detected by laser flow fluorocytometry (SPECITRUM III; manufactured by Ortho). Thus, the $KML_1$ cell was found to be $Thy1^-$, $Lyt1^-$, $Lyt2^-$ and $sIg^-$, indicating that the $KML_1$ cell is a null cell. When analyzed by using an anti-$H-2K^k$ antibody (manufactured by Litton-Bionetics), its H-2 haplotype was found to be k, demonstrating that the $KML_1$ cell is derived from MRL/l mouse. Moreover, using anti-Ia antibody (manufactured by Cedalane), the $KML_1$ cell was found to be Ia-positive. When examined by the EA rosette method, the $KML_1$ cell was found to be Fc receptor-negative ($FcR^-$).

EXPERIMENT 2

Stimulative Effect of a BCDF Solution on Antibody Production by MRL/l Mouse Spleen Cells A series of culture media were prepared by adding various amounts of the BCDF solution obtained in Example 4 to DMEM containing 5% FCS and the other additives as described above. In these culture media, spleen cells obtained from female MRL/l mice, aged 4 months, were suspended so as to give a cell density of $10^6$ cells/ml. These suspensions were placed in 25 $cm^2$ flasks (No. 25110; manufactured by Corning Glass Works) and incubated for 4 days. Then, the anti-single stranded (ss) DNA antibody titer ($A_{405}$) of the supernatant of the resulting cultures was determined. The antibody titer was expressed in terms of activity per unit amount of antibody protein ($1A_{280}$).

| Amount of supernatant of $KML_1$ cell culture added (%, v/v) | Anti-ssDNA antibody titer ($A_{405}/1A_{280}$/ml) |
| --- | --- |
| 0 | 2.06 |
| 10 | 3.92 |
| 20 | 5.04 |
| 40 | 3.94 |

As can be seen from the above results, this BCDF solution had the ability to enhance the production of anti-DNA antibodies by a factor of about 2.5.

EXPERIMENT 3

Enhancement of Antibody Production by the Mixed Culture of MRL/l Mouse Spleen Cells and $KML_1$ Cells Spleen cells obtained from female MRL/l mice, aged 4 months, and $KML_1$ cells were mixed in a culture medium and cultured at 37° C. for 2 days in an incubator having a 5% $CO_2$ atmosphere. The spleen cells were suspended at a cell density of $10^6$ cells/ml, while the $KML_1$ cells were suspended at each of the various cell densities shown in the following table. The antibody titer was expressed in the same manner as described in Experiment 2.

| Number of $KML_1$ cells added per ml | Number of MRL/l mouse spleen cells per ml | Anti-ssDNA antibody titer ($A_{405}/1A_{280}$/ml) |
| --- | --- | --- |
| 0 | $10^6$ | 5.16 |
| $10^4$ | $10^6$ | 16.46 |
| $5 \times 10^4$ | $10^6$ | 18.60 |
| $10^5$ | $10^6$ | 23.70 |
| $10^6$ | 0 | 0.64 |

As can be seen from the above results, the in vitro production of anti-ssDNA antibody was enhanced by a factor of about 5 as compared with the culture of spleen cells alone, and the degree of enhancement was higher than that achieved in Experiment 2 using a BCDF solution.

EXPERIMENT 4

Enhancement of Antibody Production by the Mixed Culture of MRL/n Mouse Spleen Cells and KML$_1$ Cells Spleen cells obtained from female MRL/n mice, aged 9 months, and KML$_1$ cells were mixed in a culture medium and cultured under the same conditions as described in Experiment 3. The spleen cells were suspended at a cell density of $10^6$ cells/ml, while the KML$_1$ cells were suspended at each of the various cell densities shown in the following table. The antibody titer was expressed in the same manner as described in Experiment 2.

| Number of KML$_1$ cells added per ml | Number of MRL/n mouse spleen cells per ml | Anti-ssDNA antibody titer ($A_{405}/1A_{280}$/ml) |
| --- | --- | --- |
| 0 | $10^6$ | 1.24 |
| $10^4$ | $10^6$ | 1.48 |
| $5 \times 10^4$ | $10^6$ | 2.80 |
| $10^5$ | $10^6$ | 2.00 |
| $10^6$ | 0 | 0.40 |

As can be seen from the above results, the in vitro production of anti-ssDNA antibody was also enhanced in MRL/n mice.

EXPERIMENT 5

Increase in the Number of Antibody-producing Cells in MRL/l Mouse Spleen Cells, by a BCDF Solution A series of culture media were prepared by adding the BCDF solution obtained in Example 5 to the serum-free medium Hybrity-1 in the various amounts shown in the following table. In each of these culture media, spleen cells obtained from male MRL/l mice, aged 5 months, were suspended so as to give a cell density of $10^6$ cells/ml and cultured for 4 days under the same conditions as described in Experiment 2.

The number of plaque forming cells (PFCs) was obtained by determining the total number of cells producing antibodies including both IgG and IgM according to the above-described procedure of Gronovicz et al. The number of ssDNA-specific PFCs was determined according to the procedure of Roder et al.

| Amount of supernatant of KML$_1$ cell culture added (%, v/v) | ssDNA-specific PFCs/ $10^6$ spleen cells* |
| --- | --- |
| 0 | 130 ± 76.8 |
| 10 | 110 ± 32.8 |
| 20 | 170 ± 65.2 |
| 40 | 330 ± 58.8 |

*Average of four mice, mean ± S.D.

As can be seen from the above results, the addition of a BCDF solution increases the number of antibody-producing cells in a unit population of spleen cells by a factor of above about 2.5, indicating a parallel relationship with the stimulative effect on antibody production as demonstrated in Experiment 2.

EXPERIMENT 6

Increase in the Total Number of Antibody-producing Cells Caused by the in vivo Administration of a BCDF Solution to BALB/c Mice Three female BALB/c mice, aged 5 months, were initially immunized intravenously with of $4 \times 10^8$ ssDNA-coated sheep red blood cells (SRBCs). This day was defined as the first day (=day 1) of the test.

On day 4, $4 \times 10^8$ ssDNA-coated SRBCs were intravenously injected again and, at the same time, 0.2 ml of a concentrated BCDF solution prepared from (in Example 6) the BCDF solution obtained in Example 5 was intraperitoneally administered to the mice.

Similarly, 0.2 ml of the concentrated BCDF solution was intraperitoneally administered to the mice on days 6 and 8.

On day 10, spleen cells were collected from the BALB/c mice and the numbers of ssDNA-specific IgG($\gamma$) PFCs and IgM($\mu$) PFCs per unit population of spleen cells were determined. Four measurements were made for each mouse.

| supernatant of KML$_1$ cell culture | ssDNA-specific PFCs/$10^6$ spleen cells* | |
| --- | --- | --- |
| | $\mu$PFCs | $\gamma$PFCs |
| + | 63.3 ± 7.5 | 787 ± 105 |
| − | 88.9 ± 35.8 | 392 ± 149 |

*Average of 12 measurements, mean ± S.D.

As can be seen from the above results, the number of $\gamma$PFCs in the mice treated with the BCDF solution was approximately doubled as compared with untreated mice. This clearly indicates that the number of antibody-producing cells can also be actually increased by in vivo administration of a BCDF solution obtained with the KML$_1$ cell line.

What is claimed is:

1. A concentrated supernatant containing a B cell differentiation factor produced by a cell line having all the identifying characteristics of cell line KML$_1$-7, deposit number 86/091801.

* * * * *

UNITED STATES PATENT AND TRADEMARK OFFICE
CERTIFICATE OF CORRECTION

PATENT NO. : 5,250,661
DATED : October 5, 1993
INVENTOR(S) : KANAI et al

It is certified that error appears in the above-indentified patent and that said Letters Patent is hereby corrected as shown below:

Title page, Item [60] last line "October 19" should read --October 9--.

Title page, Item [30] "227709" should read --60-227709--.

Signed and Sealed this

Twenty-sixth Day of July, 1994

*Attest:*

BRUCE LEHMAN

*Attesting Officer*     *Commissioner of Patents and Trademarks*